United States Patent
Johnson et al.

(10) Patent No.: US 9,268,913 B2
(45) Date of Patent: Feb. 23, 2016

(54) MEDICATION MANAGEMENT SYSTEM AND METHOD

(71) Applicant: KONINKLIJKE PHILIPS N.V., Eindhoven (NL)

(72) Inventors: Mark Thomas Johnson, Eindhoven (NL); Raymond Van Ee, Eindhoven (NL); Joyca Petra Wilma Lacroix, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/347,264

(22) PCT Filed: Oct. 8, 2012

(86) PCT No.: PCT/IB2012/055418
§ 371 (c)(1),
(2) Date: Mar. 26, 2014

(87) PCT Pub. No.: WO2013/054245
PCT Pub. Date: Apr. 18, 2013

(65) Prior Publication Data
US 2014/0236352 A1    Aug. 21, 2014

Related U.S. Application Data

(60) Provisional application No. 61/545,607, filed on Oct. 11, 2011.

(30) Foreign Application Priority Data

Oct. 11, 2011  (EP) ..................................... 11184593

(51) Int. Cl.
*G08B 5/00* (2006.01)
*G06F 19/00* (2011.01)
(Continued)

(52) U.S. Cl.
CPC ........... *G06F 19/3462* (2013.01); *A61J 7/0409* (2013.01); *A61J 7/0481* (2013.01);
(Continued)

(58) Field of Classification Search
CPC .......................... G04G 11/00; G04G 19/3456
USPC ............ 340/815.43, 573.1, 540, 541, 539.12, 340/501; 700/242, 244, 231, 233, 236
See application file for complete search history.

(56) References Cited

U.S. PATENT DOCUMENTS 4,926,572 A    5/1990 Holmes
5,646,912 A *  7/1997 Cousin ............................ 368/10
(Continued)

FOREIGN PATENT DOCUMENTS

CN    201350222 Y    11/2009
SE    200601634 A    2/2008
(Continued)

OTHER PUBLICATIONS

C.L. Wiggs et al., "Properties and Mechanisms of Perceptual Priming", Cognitive Neuroscience, vol. 8, Issue 2, Apr. 1998, pp. 227-233.
(Continued)

*Primary Examiner* — Tai T Nguyen

(57) ABSTRACT

A medication management system (100) comprises a portable device (10) attachable to a user (30) and a medication dispenser (20). The portable device comprises a lighting means (50) for providing a visual stimulus (55) to indicate an approaching medication intake moment or period. The medication dispenser (20) comprises further lighting means (40, 41) for providing a further visual stimulus (45) to draw the attention of the user. The visual stimulus and the further visual stimulus have a same predetermined color and the visual stimulus (55) is provided a predetermined time before the medication dispenser provides the further visual stimulus (45).

15 Claims, 6 Drawing Sheets

(51) Int. Cl.
*G04G 11/00* (2006.01)
*A61J 7/04* (2006.01)
*A61J 7/00* (2006.01)

(52) U.S. Cl.
CPC .............. *G04G 11/00* (2013.01); *A61J 7/0084* (2013.01); *A61J 7/0418* (2015.05); *A61J 7/0454* (2015.05); *A61J 2007/0418* (2013.01); *A61J 2200/30* (2013.01); *A61J 2205/20* (2013.01)

(56) References Cited

U.S. PATENT DOCUMENTS

| | | | |
|---|---|---|---|
| 7,107,122 | B1 | 9/2006 | Whyte |
| 7,545,257 | B2 * | 6/2009 | Brue ........................ 340/309.16 |
| 7,573,371 | B1 | 8/2009 | Miller |
| 8,963,707 | B2 * | 2/2015 | Bevel ........................ 340/539.12 |
| 2008/0027291 | A1 | 1/2008 | Williams-Hartman |
| 2009/0040874 | A1 * | 2/2009 | Rooney et al. .................. 368/10 |
| 2010/0214877 | A1 | 8/2010 | Turk |

FOREIGN PATENT DOCUMENTS

| | | |
|---|---|---|
| WO | WO9505143 | 2/1995 |
| WO | 2006069778 A2 | 7/2006 |

OTHER PUBLICATIONS www.epill.com, Downloaded Jun. 15, 2015, pp. 1-3.
Leech et al, "Analogy as Relational Priming: A Developmental and Computational Perspective on the Origins of a Complex Cognitive Skill", Behavioral and Brain Sciences, vol. 31, 2008, pp. 357-414.
Azrin et al, "Behavioral Engineering: The Use of Response Priming to Improve Prescribed Self-Medication", Journal of Applied Behavior Analysis, vol. 2, No. 1, 1969, pp. 39-42.

* cited by examiner

MEDICATION MANAGEMENT SYSTEM AND METHOD

CROSS-REFERENCE TO PRIOR APPLICATIONS

This application is the U.S. National Phase application under 35 U.S.C. §371 of International Application Serial No. PCT/IB2012/055418, filed on Oct. 8, 2012, 2012, which claims the benefit of U.S. Application Ser. No. 61/545,607, filed Oct. 11, 2011 and European Application Serial No. 11184593.9, filed on Oct. 11, 2011. These applications are hereby incorporated by reference herein.

FIELD OF THE INVENTION

The invention relates to a medication management system and method.

BACKGROUND TO THE INVENTION

Programmable pill dispensers are known in the art. Such a pill dispenser may have a display to provide a visual reminder signal to the user to indicate that according to a preprogrammed schedule a medication should be taken thereby helping the user to prevent forgetting to take the medications at the moment prescribed by the doctor. Due to the size of the pill dispenser the user may not be able to continuously carry the dispenser with him when for example he moves around the house. Therefore it is common use that the pill dispenser is positioned at a frequently visited location somewhere in the user's house. This may result in the user failing to see a visual reminder signal to take his medication when he is out of the room where the pill dispenser is located, or the user forgetting to check the pill dispenser's display for the presence of the reminder signal when he returns to said room.

SUMMARY OF THE INVENTION

According to a first aspect of the invention there is provided a medication management system according to claim 1. As an example when the user is in the living room while the medication dispenser is located in the kitchen, the visual reminder signal from the medication dispenser may not reach him. In the system according to claim 1 the lighting means included in the portable device provides a visual stimulus to the user to indicate the approaching medication intake moment or period. In the invention the visual stimulus is presented by the portable device, which is worn by the user. This enables the user to take notice of the visual stimulus also when not being in the vicinity of the medication dispenser. After receiving the visual stimulus the user may move to the kitchen. The invention is further based on the insight that by using perceptual priming an increased effect of a notification to take prescribed medication may be obtained. Therefore the further lighting means included in the medication dispenser provides a further visual stimulus to the user to draw the attention of the user to take the prescribed medication. For example the further visual stimulus provided to the user may be used to draw the attention of the user to the location of the medication dispenser and thereby of the medication that has to be taken. It is hypothesized that by using the same predetermined color the visual stimulus and the further visual stimulus will be processed by the same neural pathways in the brain, which makes the further visual reminder stimulus increasingly effective in notifying the user to take his prescribed medication. For background information on perceptual priming reference is made to "Properties and mechanisms of perceptual priming", Cheri L. Wiggs and Alex Martin, Current Opinion in Neurobiology, Volume 8, Issue 2, April 1998, pages 227-233. Continuing with the example, after having taken notice of the visual stimulus from the portable device the user may move to the kitchen but be distracted by other items and events such as for example sounds from the television in the living room. After arrival in the kitchen the user observes the medication dispenser providing a further visual stimulus having the same predetermined color as the visual stimulus provided by the portable device thereby effectively engaging already primed neural pathways that facilitate the user to take his medication. For example the medication dispenser may comprise a LED (Light Emitting Diode) providing yellow light in correspondence with an intake moment or period included in the predetermined medication schedule. A display on the portable device carried by the user provides a yellow visual stimulus a predetermined time before the corresponding further visual stimulus by the LED is provided. By providing the visual stimulus earlier than the further visual stimulus the user is made more susceptible for the predetermined color of the further visual stimulus, thereby improving the adherence to the medication schedule.

In an embodiment the medication dispenser is arranged to provide more than one medication wherein each medication has a corresponding predetermined color for indicating the intake moment or time period to the user. The lighting means of the portable device and the further lighting means of the medication dispenser are arranged to provide a plurality of colors to enable that the visual stimulus and the further visual stimulus have said predetermined color. The medication schedule defining the time periods in which a medication should be taken may for example prescribe that in the morning a user should take a first medication, indicated to the user with a yellow visual and further visual stimulus, and in the evening the patient should take a second medication, indicated with a red visual and further visual stimulus. The lighting means of the portable device are arranged to provide the yellow and red visual stimulus in dependence of the medication schedule of said user. In a first embodiment the medication dispenser may be a pill box having two separate compartments, one compartment having a lid with a yellow LED and storing the first medication and the other compartment having another lid with a red LED and storing the second medication. In a second embodiment the medication dispenser has a display capable of providing a yellow light when the first medication is provided and a red light when the second medication is provided.

In a further embodiment the medication dispenser is arranged to provide more than one medication for more than one user, wherein each medication has a corresponding predetermined color for indicating the intake time period to the corresponding user. The further lighting means of the medication dispenser are arranged to provide for each medication the further visual stimulus having the corresponding predetermined color. For example the medication schedule of a first user prescribes that in the morning a first medication should be taken, indicated to the first user with a yellow visual and further visual stimulus, whereas a further medication schedule of a second user prescribes to take in the evening a second medication, indicated with a red visual and further visual stimulus. The lighting means of the portable device of the first user is arranged to provide the yellow stimulus in dependence of the medication schedule of the first user whereas the portable device of the second user is arranged to provide the red visual stimulus in dependence of the further medication schedule of the second user. In a first embodiment the medication dispenser may have two separate compartments for storing medication for a first and second user, a first compartment having a first lid with a yellow LED and storing the first medication and a second compartment having a second lid with a red LED and storing the second medication. In a second embodiment the medication dispenser has a display capable of providing a yellow light when the first medication is provided and a red light when the second medication has to be taken.

In a further embodiment of the medication management system the medication dispenser is arranged to allow access to a medication stored in the dispenser only when the further lighting means provides the further visual stimulus. This prevents the taking of medication outside the time window prescribed by the medication schedule.

In a further embodiment of the medication management system the medication dispenser further comprises detection means to detect the presence of the portable device within a predetermined range from said medication dispenser, wherein the further lighting means only provide the further visual stimulus when the presence of the portable device in said predetermined range is detected. The predetermined range corresponds preferably to the area around the medication dispenser from which the user can observe the further visual stimulus. This reduces power consumption by the further lighting means in the dispenser when the portable device is outside the predetermined range, which is advantageous in case of a battery supplied medication dispenser.

In a further embodiment of the medication management system the portable device further comprises vibration means to provide a tactile stimulus to the user wherein the tactile stimulus is provided before or simultaneously with the visual stimulus. In case the portable device is attached to the wrist, or is carried as a pendant, the user may occasionally not observe the visual stimulus. The tactile stimulus will trigger the user to look at the portable device and enable the user to take notice of the visual stimulus. In a further embodiment the portable device comprises audio means to provide an audible stimulus to the user, wherein the audible stimulus acts as the trigger to look at the portable device. In a further embodiment the portable device comprises both said vibration means and said audio means.

According to a second aspect of the invention there is provided a method of medication management according to any one of claims 8-13.

In a further embodiment the method further comprises the step of providing with vibration means comprised in the portable device a tactile stimulus before or simultaneous with the visual stimulus.

BRIEF DESCRIPTION OF THE DRAWINGS

Exemplary embodiments of the invention will now be described, by way of example only, with reference to the following drawings, in which.

DETAILED DESCRIPTION OF THE EMBODIMENTS

Figure 1:
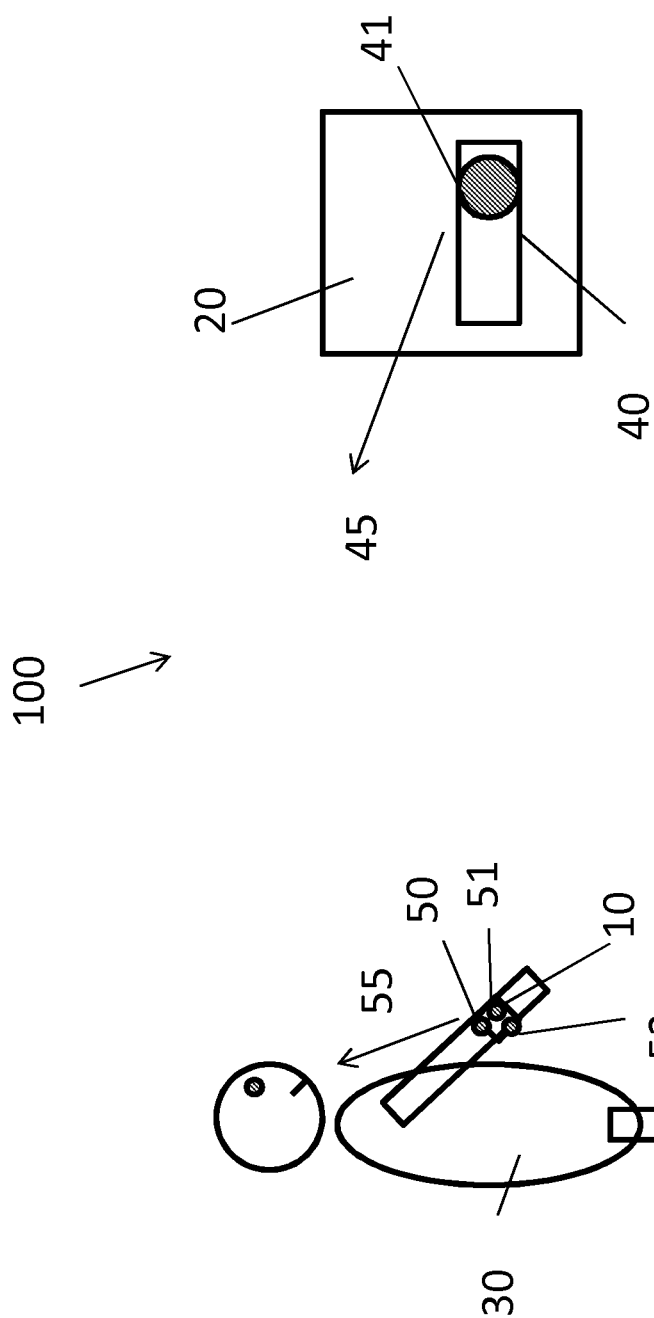
FIG. 1 shows an embodiment of a medication management system.

FIG. 1 shows a medication management system 100 that comprises a portable device 10 and a medication dispenser 20. The portable device is attachable to the user 30 and may for example be shaped as a watch that is attached to the wrist or may be carried with a strap around the neck as a pendant. The portable device accompanies the user whereas in use the medication dispenser may be located somewhere in the house, for example in the kitchen. This means that the user may not always be in the vicinity of the medication dispenser when he is engaged in the activities of daily living. The portable device 10 may comprise a memory storing the medication schedule which comprises data on the medication intake moments or time periods for that user. The medication may comprise more than one medicine; for example a medical doctor may prescribe that the user 30 has to take in the morning a first medicine and in the afternoon a second medicine. The portable device further comprises lighting means 50 to provide a visual stimulus 55 to the user in dependence of the user's medication schedule. This visual stimulus is provided in advance of the scheduled and prescribed intake moment or period to indicate the upcoming intake moment for a prescribed medication. When the user during his daily activities observes the visual stimulus 55 a neural pathway in his brain is activated which makes him more 'sensitive' (i.e. the user's brain is primed) for a further visual stimulus 45 that has the same predetermined color. This further visual stimulus 45 is provided by further lighting means 40, 41 included in the medication dispenser 20. For example the lighting means (LED, display, etc.) in the portable device 10 may provide the user a visual stimulus 55 with a yellow colored light. When the user enters the kitchen and receives the further visual stimulus 45 with a yellow colored light he is reminded to take the medication. It is hypothesized that the yellow color of the further visual stimulus is processed in the brain through the same neural pathway as the earlier provided visual stimulus, that is the neural pathway is primed (with the predetermined yellow priming color), thereby making the further visual stimulus increasingly effective in reminding the user to take his medication.

The further lighting means 41 provide the further visual stimulus in dependence of the medication schedule that may be stored in another memory included in the medication dispenser 20. Further the medication dispenser 20 may be arranged to provide only access to the medication in the dispenser 20 when and as long as the further visual stimulus 45 is provided so that the user can only take the medicine in compliance with the prescribed medication schedule. The medication dispenser may be portable and battery powered. To increase battery life the medication dispenser 20 may comprise detection means (not shown) to detect the presence of the user within a predetermined range. Only when the user is detected the further lighting means 40 provides the further visual stimulus 45 to the user, thereby saving on battery energy consumption. The detection means may for example be a PIR (Passive Infrared) motion detector.

When the portable device 10 is attached to the wrist the user 30 may not observe the visual stimulus 55. Therefore the portable device 10 may comprise further means 51, 52 to trigger the user to check the portable device and when doing so receive the visual stimulus 55. For example the portable device may comprise vibration means 51 to provide a tactile stimulus which is an unobtrusive way to gain attention from the user. The portable device may instead of or in addition to the vibration means also have audio means 52 to provide an audible stimulus. The tactile and/or audible stimulus may be provided before or simultaneous with the visual stimulus 55.

Figure 2:
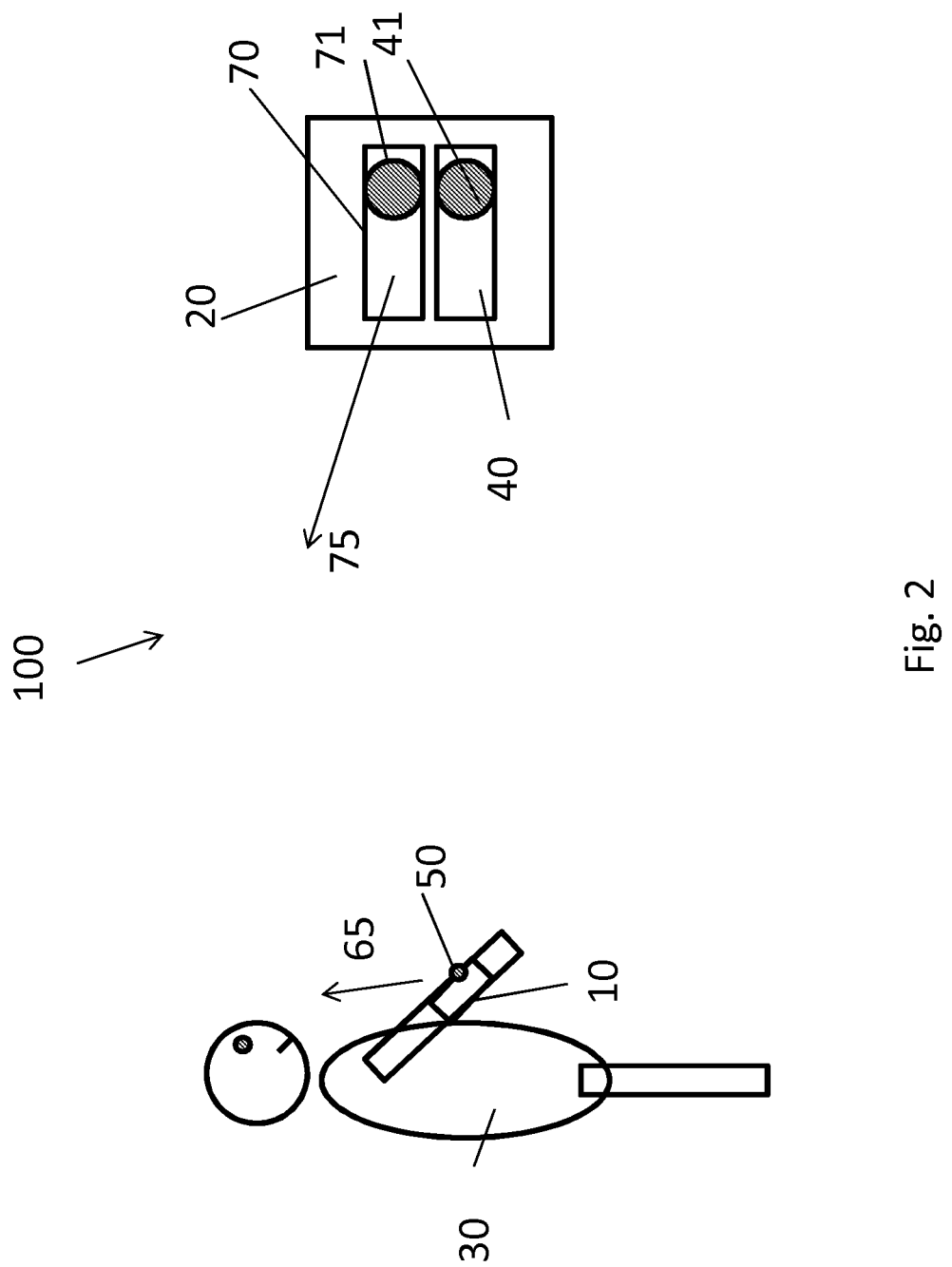
FIG. 2 shows a further embodiment of a medication management system.

A further embodiment of the medication system 100 is shown in FIG. 2. In this medication system the portable device 10 and the medication dispenser 20 are adapted to a more complex medication schedule in which the user 30 is for example prescribed to take a first medicine in the morning and a second medicine in the evening. The lighting means 50 in the portable device 10 is arranged to provide a first visual stimulus 55 with a first predetermined color to indicate an approaching intake period for the first medicine and a second visual stimulus 65 with a second predetermined color to indicate an approaching medicine intake period for the second medicine, the first and second visual stimulus being provided in dependence of said medication schedule.

The further lighting means 40, 70 included in the medication dispenser provide the corresponding first further visual stimulus 45 and second further visual stimulus 75. The further lighting means may comprise two separate lighting means or, alternatively, comprise a single lighting means capable of providing a plurality of colors such that the further lighting means are capable to provide the corresponding first further visual stimulus 45 and second further visual stimulus 75. Further the medication dispenser 20 may be arranged to provide only access to the first medicine in the dispenser 20 when and as long as the first further visual stimulus is provided and to the second medicine as long as the second further visual stimulus is provided to make sure that the user takes the right medicine and acts in compliance with the prescribed medication schedule. Further the medication dispenser 20 may have detection means (not shown) to detect the presence of the user within a predetermined range. The portable device may further comprise vibration and/or audio means to trigger the user to check the portable device as discussed earlier.

Figure 3:
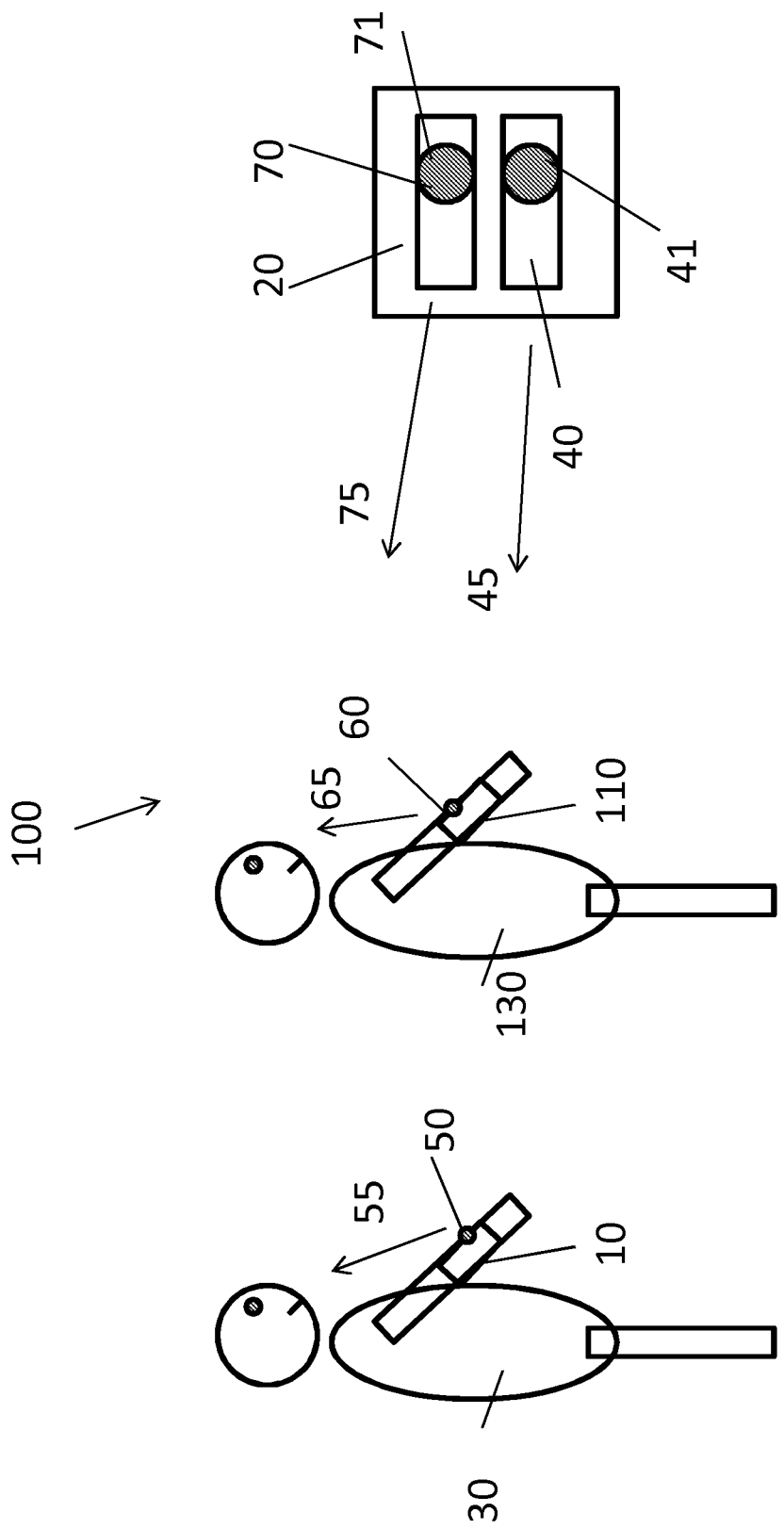
FIG. 3 shows a medication management system for two users.

FIG. 3 shows a further embodiment of a medication system 100 that is configured for more than one user. The medication system 100 comprises a medication dispenser 20 that is arranged to store the medication for a first user 30 carrying a first portable device 10 and a second user 130 carrying a second portable device 110. The first lighting means 50 of the first portable device 10 is arranged to provide a first visual stimulus 55 having the first predetermined color corresponding with the first further visual stimulus provided by the first access point 40 having first further lighting means for providing the first predetermined color. Likewise the second lighting means 60 of the second portable device 110 is arranged to provide a second visual stimulus 65 having the second predetermined color corresponding with the second further visual stimulus provided by the second access point 40 having second further lighting means for providing the second predetermined color. Or, alternatively, the further lighting means are capable of providing a plurality of colors such that the further lighting means are capable to provide the corresponding first further visual stimulus 45 and second further visual stimulus 75. This embodiment may further also comprise the feature of restricted access in time to the medication stored in the dispenser, similar as discussed earlier. In the embodiment of FIG. 3 the detection means of the medication dispenser may be further arranged to detect and identify the presence of a user in a predetermined range, for example by using an RF ID, to enable that access to the medication is further restricted to the user for which said medication was prescribed preventing for example that the first user accidently takes at his prescribed medication intake moment the medication that was prescribed for the second user.

Figure 4:
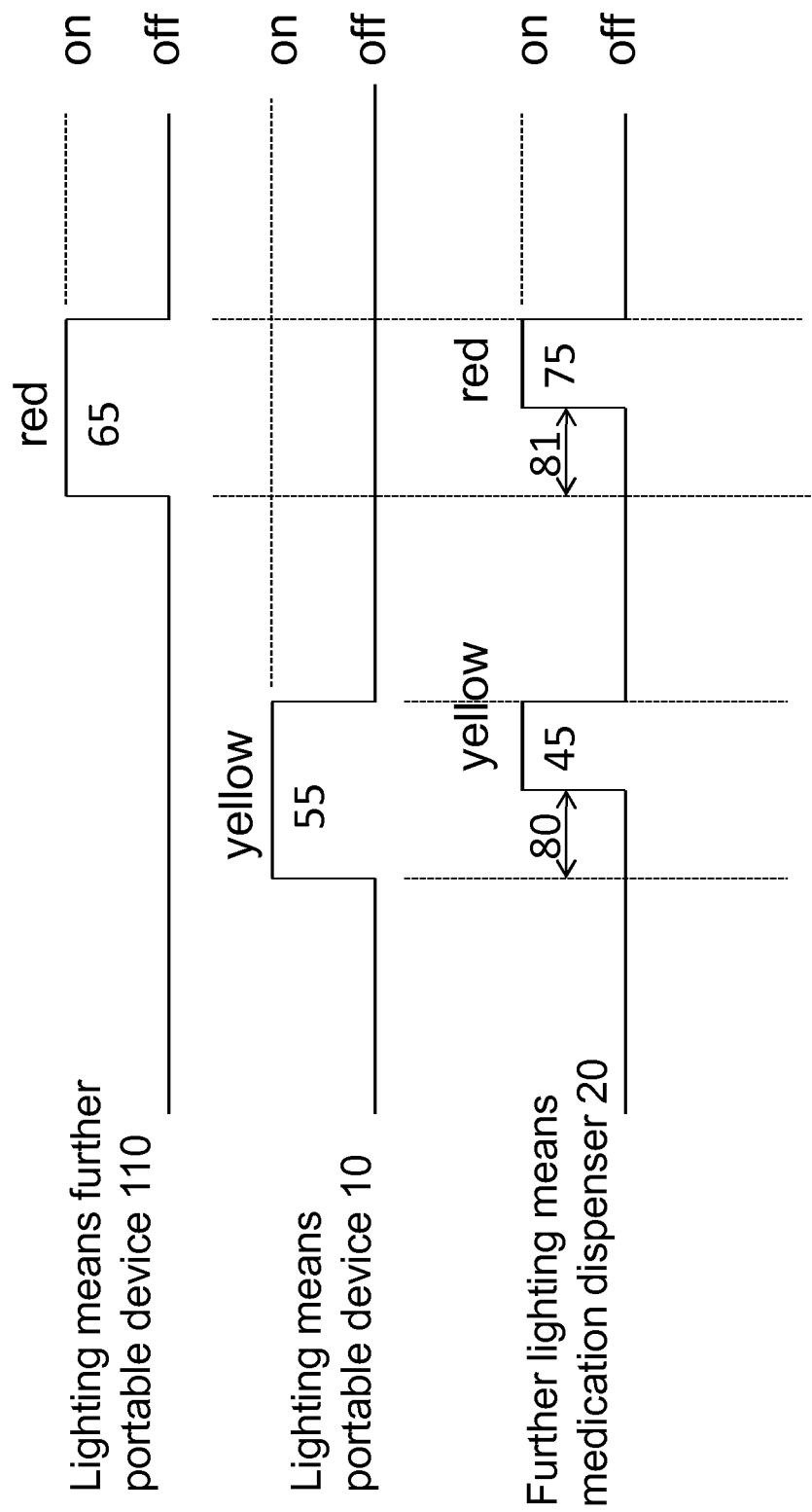
FIG. 4 shows a timing diagram.

FIG. 4 shows for the medication system of FIG. 3 an example of a timing diagram for the first and second visual stimulus 55, 65 provided by the (lighting means included in the) first and second portable device 10, 110 and the corresponding first and second further visual stimulus 45, 75 provided by the (further lighting means included in the) medication dispenser 20. This timing diagram is derived from the medication schedule that is prescribed for the first and second user. The first lighting means 50 in the first portable device 10 is arranged to provide the first visual stimulus 55 to the first user 30 a predetermined time 80 before the corresponding first further visual stimulus 45 is provided by the medication dispenser 20. The first visual stimulus and the first further visual stimulus may for example be yellow. During the time that the first further stimulus 45 is provided only the first user 30 has access to his/her prescribed medication. Likewise the second lighting means 60 in the second portable device 110 provides the second user 130 a second visual stimulus 65, for example colored red, a predetermined time 81 before the corresponding second further visual stimulus 75 (having the same color as the second visual stimulus) is provided, and during the time that the second further stimulus 75 is provided only the second user 130 has access to his/her prescribed medication.

In a further embodiment the medication dispenser 20 is further arranged to exchange data with a remote caregiver via the Internet to allow updating and changing of the medication schedule and monitoring of the adherence of the user to the prescribed medication schedule. In a further embodiment of the medication system 100 the portable device 10 and the medication dispenser 20 further comprise data transmission means to enable a wireless coupling between the portable device 10, 110 and the medication dispenser 20. This provides the advantage that the portable device may receive an updated medication schedule from the medication dispenser and timing settings for the visual signals that indicate an approaching scheduled medication intake moment or period. This timing setting may comprise (see FIG. 5) data on an "on time" 90 in which a higher intensity visual stimulus 55 is provided and an "off time" 91 in which a lower intensity visual stimulus is provided, and on the predetermined time 93 between the activation of the visual stimulus and the activation of the further visual stimulus 45 (which is dependent on the medication schedule provided by the caregiver). Further the lighting means 50 included in the portable device 10 and the further lighting means 41 included in the medication dispenser 20 may be arranged to provide a plurality of predetermined colors, wherein the predetermined color that is used for the visual stimulus 55 and further visual stimulus 45 is programmable by a caregiver. When for example the medication schedule is changed and the user has to take two different types of medication instead of only one type the caregiver can program the portable device and the medication dispenser to provide two different predetermined colors.

Figure 5:
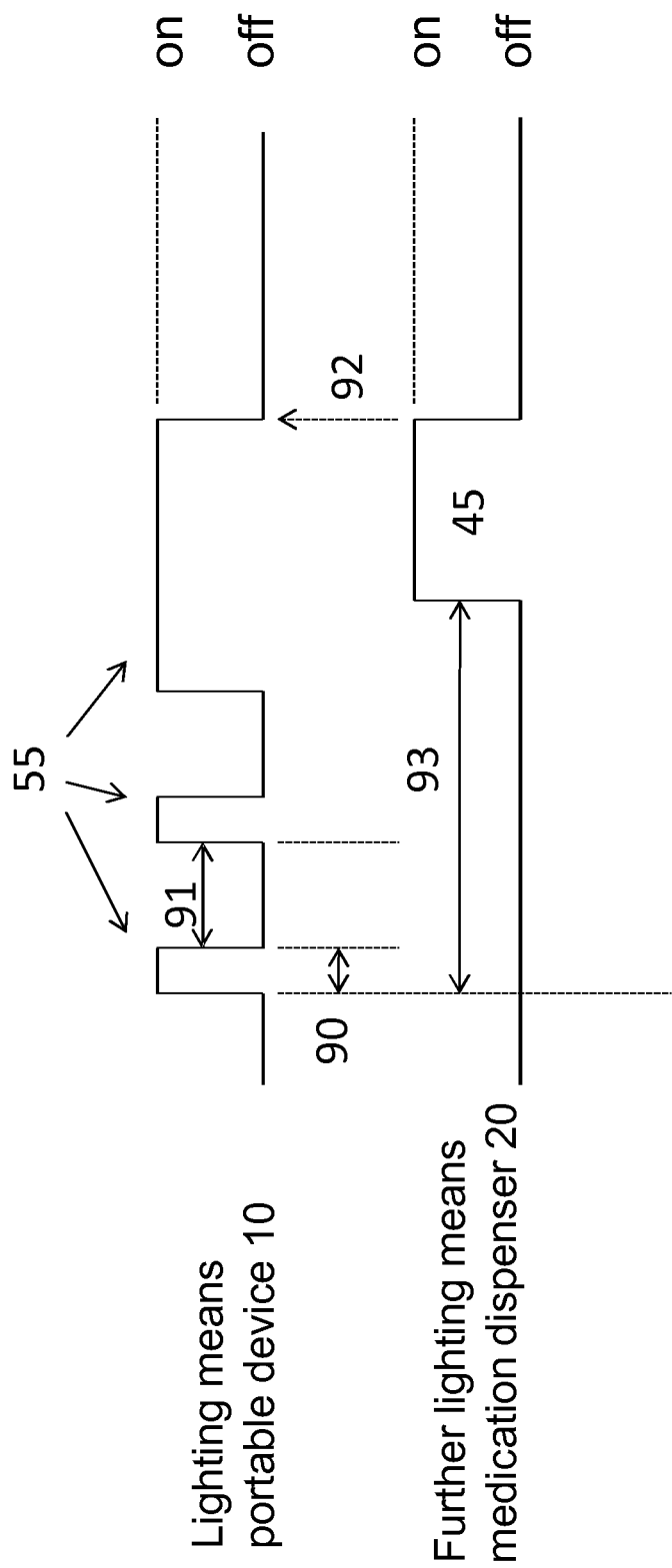
FIG. 5 shows a further timing diagram.

FIG. 5 shows a further timing diagram of the visual stimulus 55 provided by the lighting means 50 of the portable device 10 and the further visual stimulus 45 provided by the further lighting means 41 included in the medication dispenser 20. The lighting means may be arranged to provide a pulsating visual stimulus 55 having an "on time" 90 in which a higher intensity visual stimulus is provided and an "off time" 91 in which a lower intensity visual stimulus is provided. In an embodiment the "on-time" is preferably about 10 seconds, or more than 10 seconds and the "off time" preferably is about 5 minutes or less. In a further embodiment the medication dispenser 20 is arranged to detect when the user 30 has taken the medication from the dispenser and in response thereto signals 92 the portable device 10 to switch off the visual stimulus as the prescribed medication has been taken.

Figure 6:
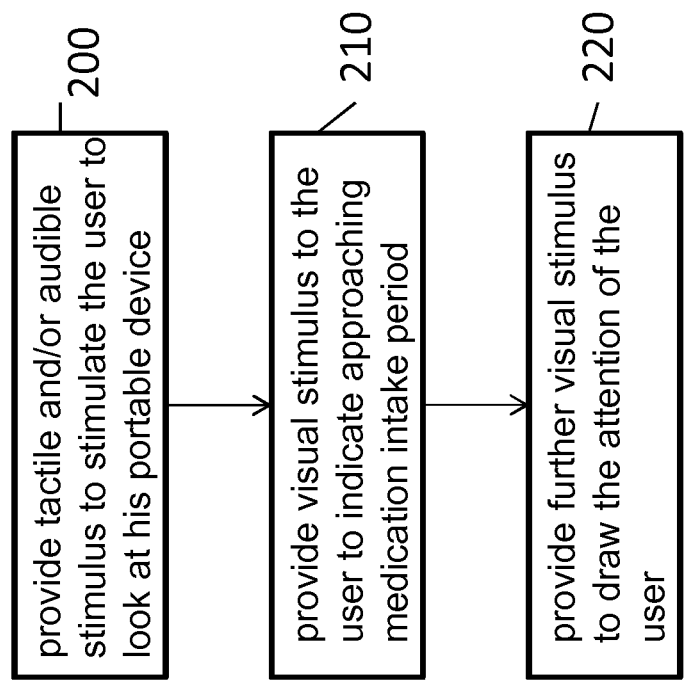
FIG. 6 shows an embodiment of a medication management method.

FIG. 6 shows an embodiment of a medication management method comprising the step 210 of providing a visual stimulus 55, 65 to a user 30, 130 to indicate an approaching predetermined medication intake moment or period and the further step 220 of providing a further visual stimulus 45, 75 to draw the attention of the user (for example to the location of the medication dispenser 20) and to remind the user of taking the medicine, wherein the visual and further visual stimulus have the same predetermined color. The visual stimulus is provided by a lighting means 50, 60 included in a portable device 10, 110 that is carried by the user 30, 130 so that independent of the location of the user relative to the location of the medication dispenser the user can receive the visual stimulus 55 in dependence of a prescribed medication schedule. The portable device 10 may for example be carried at the wrist like a watch, or with a cord around the neck as a pendant. The further visual stimulus is provided by means 40, 41, 70, 71 included in the medication dispenser.

In a further embodiment the portable device is a smart phone having a color display, the smart phone being programmed to provide the visual stimulus 55 in dependence of a programmed medication schedule.

To make the user 10 aware of the further visual stimulus 45, for example when the smart phone is carried in a pocket, the method may comprise a first step 200 of providing a tactile stimulus and/or audible stimulus before or simultaneous with the visual stimulus 55. For example the smart phone may comprise vibration means 51 that provide a tactile stimulus to the user. In response thereto the user may check his/her phone and observe the visual stimulus 55.

In an embodiment the medication dispenser 20 is a medication bottle having a lid with further lighting means that partly or completely colors the lid with the predetermined color, for example yellow. The visual stimulus 55 having the same predetermined color (in this example yellow) and the further visual stimulus 45 provided by the yellow colored lid use a same neural pathway in the brain of the user 30. The visual stimulus 55 is 'remembered' in the brain, making it more sensitive for a following further visual stimulus 45. The visual stimulus is provided a predetermined time 93 before the scheduled intake time at which the further visual stimulus is provided. In case the visual stimulus is not continuously provided until the end of the scheduled medication intake period (such as for example in FIG. 4) but is instead a pulse signal (having an "on time" 90 in which a higher intensity visual stimulus is provided and an "off time" 91 in which a lower intensity visual stimulus is provided) providing the user with a visual stimulus for a limited amount of time (indicated with 90 in FIG. 5) said visual stimulus 55 should be provided for at least 10 seconds and about 5 minutes or less before the further visual stimulus 45 is provided.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A medication management system comprising:
   a portable device attachable to a user, the portable device comprising a lighting means arranged to provide a visual stimulus having a predetermined color to indicate an approaching medication intake moment or period; and
   a medication dispenser that is physically separate and distinct from the portable device comprising a further lighting means arranged to provide a further visual stimulus that provides light with the predetermined color to draw attention of the user and further arranged to indicate the medication intake moment or period;
   wherein the portable device is arranged to provide with the lighting means the visual stimulus a predetermined time before the medication dispenser provides with the further lighting means the corresponding further visual stimulus.

2. A medication management system according to claim 1, wherein the portable device is worn by the user and the medication dispenser is not worn by the user.

3. A medication management system comprising:
   a portable device attachable to a user, the portable device comprising a lighting means arranged to provide a visual stimulus having a predetermined color to indicate an approaching medication intake moment or period; and
   a medication dispenser comprising a further lighting means arranged to provide a further visual stimulus that provides light with the predetermined color to draw attention of the user and further arranged to indicate the medication intake moment or period;
   wherein the portable device is arranged to provide with the lighting means the visual stimulus a predetermined time before the medication dispenser provides with the further lighting means the corresponding further visual stimulus, and
   wherein the medication dispenser is arranged to provide to the user at least two different types of medication, each of them being indicated with its own predetermined color.

4. A medication management system according to claim 3, wherein the further lighting means comprise a first further lighting means and a second further lighting means, the medication dispenser comprising a first container for storing a first medication and a second container for storing a second medication, the first container comprising the first further lighting means, the first further lighting means configured to provide a first further visual stimulus to indicate the medication intake moment or period of the first medication, and the second container comprising the second further lighting means, the second further lighting means configured to provide the second further visual stimulus to indicate the medication intake moment or period of the second medication.

5. A medication management system according to claim 3, wherein the medication dispenser is arranged to allow access to the medication only when the further lighting means provides the further visual stimulus.

6. A medication management system according to claim 3, wherein the medication dispenser further comprises detection means to detect presence of the portable device within a predetermined range from said medication dispenser, the further lighting means being further arranged to provide the further visual stimulus only when the presence of the portable device in said predetermined range is detected.

7. A medication management system according to claim 3, wherein the portable device further comprises one or both of vibration means that provide a tactile stimulus to the user, or audio means that provide an audible stimulus to the user, wherein one or both of the tactile stimulus or the audible stimulus is provided before or simultaneous with the lighting means providing the visual stimulus.

8. A medication management system according to claim 3, wherein the further lighting means are arranged to provide a plurality of further visual stimuli with a corresponding plurality of predetermined colors, and the medication management system further comprises a plurality of portable devices, each comprising a lighting means for providing a visual stimulus having a predetermined color corresponding to a different one of the plurality of predetermined colors.

9. A method of medication management comprising:
providing, with a lighting means included in a portable device that is attachable to a user, a visual stimulus to said user, the visual stimulus having a predetermined color to indicate an approaching medication intake moment or period; and
providing, with a further lighting means included in a medication dispenser that is physically separate and distinct from the portable device, a further visual stimulus to the user to draw attention of the user and to indicate the medication intake moment or period, the further visual stimulus having the predetermined color, the predetermined color configured to draw the attention of the user,
wherein the lighting means provides the visual stimulus a predetermined time before the further lighting means provides a corresponding further visual stimulus.

10. The method of medication management of claim 9, wherein the visual stimulus is provided while the portable device is worn by the user and the further visual stimulus is provided while the medication dispenser is not worn by the user.

11. A method of medication management comprising:
providing, with a lighting means included in a portable device that is attachable to a user, a visual stimulus to said user, the visual stimulus having a predetermined color to indicate an approaching medication intake moment or period;
providing, with a further lighting means included in a medication dispenser, a further visual stimulus to the user to draw attention of the user and to indicate the medication intake moment or period, the further visual stimulus having the predetermined color, the predetermined color configured to draw the attention of the user,
wherein the lighting means provides the visual stimulus a predetermined time before the further lighting means provides a corresponding further visual stimulus;
providing, with the lighting means included in the portable device a first visual stimulus having a first predetermined color and providing, with the further lighting means included in the medication dispenser, a first further visual stimulus having the first predetermined color to indicate an approaching medication intake moment or period of a first medication, and providing, with the lighting means included in the portable device, a second visual stimulus having a second predetermined color and providing, with the further lighting means included in the medication dispenser, a second further visual stimulus having the second predetermined color to indicate an approaching medication intake moment or period of a second medication.

12. The method of medication management according to claim 11, further comprising allowing access to medication stored in the medication dispenser when the medication dispenser provides the further visual stimulus.

13. The method of medication management according to claim 11, further comprising of detecting presence of the portable device in a predetermined range from the medication dispenser, providing the further visual stimulus being dependent on the detected presence of the portable device in the predetermined range.

14. The method of medication management according to claim 11, further comprising providing, with the portable device, a tactile or audible stimulus to the user before or simultaneous with the visual stimulus.

15. A method of medication management comprising:
providing, with a lighting means included in a portable device that is attachable to a user, a visual stimulus to said user, the visual stimulus having a predetermined color to indicate an approaching medication intake moment or period; and
providing, with a further lighting means included in a medication dispenser, a further visual stimulus to the user to draw attention of the user and to indicate the medication intake moment or period, the further visual stimulus having the predetermined color, the predetermined color configured to draw the attention of the user,
wherein the lighting means provides the visual stimulus a predetermined time before the further lighting means provides a corresponding further visual stimulus;
providing, with a first lighting means included in a first portable device that is attachable to a first user, a first visual stimulus to said first user, the first visual stimulus having a first predetermined color to indicate an approaching medication intake moment or period for the first user;
providing, with a second lighting means included in a second portable device that is attachable to a second user, a second visual stimulus to said second user, the second visual stimulus having a second predetermined color to indicate an approaching medication intake moment or period for the second user;
providing, with the further lighting means included in the medication dispenser, a first further visual stimulus to the first user, the first further visual stimulus having the first predetermined color to draw the attention of the first user;
providing, with the further lighting means included in the medication dispenser a second further visual stimulus to the second user, the second further visual stimulus having the second predetermined color to draw the attention of the second user;
wherein the first lighting means provides the first visual stimulus a first predetermined time before the medication dispenser provides the corresponding first further visual stimulus to the first user, and wherein the second lighting means provides the second visual stimulus a second predetermined time before the medication dispenser provides the corresponding second further visual stimulus to the second user.

* * * * *